(12) United States Patent
Young et al.

(10) Patent No.: US 8,814,786 B2
(45) Date of Patent: Aug. 26, 2014

(54) GUIDING DEVICE FOR USE WITH LARYNGOSCOPE

(75) Inventors: Peter Young, Kings Lynn (GB); Anil Patel, Surrey (GB)

(73) Assignee: Indian Ocean Medical Inc., Mahe (SC)

( * ) Notice: Subject to any disclaimer, the term of this patent is extended or adjusted under 35 U.S.C. 154(b) by 0 days.

(21) Appl. No.: 13/126,777

(22) PCT Filed: Oct. 29, 2009

(86) PCT No.: PCT/GB2009/002578
§ 371 (c)(1),
(2), (4) Date: Aug. 30, 2011

(87) PCT Pub. No.: WO2010/049694
PCT Pub. Date: May 6, 2010

(65) Prior Publication Data
US 2011/0306839 A1    Dec. 15, 2011

(30) Foreign Application Priority Data

Oct. 30, 2008    (GB) .................................. 0819942.4

(51) Int. Cl.
*A61B 1/267*    (2006.01)
*A61B 1/00*    (2006.01)

(52) U.S. Cl.
CPC ............. *A61B 1/267* (2013.01); *A61B 1/00135* (2013.01); *A61B 1/00105* (2013.01); *A61B 1/0014* (2013.01); *A61B 1/00052* (2013.01)
USPC ....................................................... 600/188

(58) Field of Classification Search
USPC .................. 600/186, 188, 190, 191, 193, 194
See application file for complete search history.

(56) References Cited

U.S. PATENT DOCUMENTS

| | | | |
|---|---|---|---|
| 3,426,749 A | 2/1969 | Jephcott |
| 4,337,761 A | 7/1982 | Upsher |
| 4,574,784 A | 3/1986 | Soloway |
| 4,579,108 A | 4/1986 | Bauman |
| 4,834,077 A | 5/1989 | Sun |
| 5,261,392 A | 11/1993 | Wu |
| 5,347,995 A | 9/1994 | Slater et al. |
| 5,349,943 A | 9/1994 | Ruiz |
| 5,381,787 A | 1/1995 | Bullard |

(Continued)

FOREIGN PATENT DOCUMENTS

| | | | |
|---|---|---|---|
| CN | 2870731 Y | 1/2006 |
| CN | 201194790 Y | 2/2009 |

(Continued)

OTHER PUBLICATIONS

Patent Examination Report No. 1 in Application No. 2009309483, Applicant: Indian Ocean Medical Inc., IP Australia, Oct. 3, 2013.

(Continued)

*Primary Examiner* — Pedro Philogene
*Assistant Examiner* — David Comstock
(74) *Attorney, Agent, or Firm* — Ostrager Chong Flaherty & Broitman P.C.

(57) ABSTRACT

A guiding device for use with a laryngoscope for assisting in the insertion of an endotracheal tube into a patient, the device comprising a guiding means for guiding an endotracheal tube through the patient's upper airways, and an attachment means to attach the guiding means to the blade of the laryngoscope. A laryngoscope comprising the guiding device is also disclosed.

19 Claims, 7 Drawing Sheets

(56) References Cited

U.S. PATENT DOCUMENTS

| | | |
|---|---|---|
| 2003/0168059 A1 | 9/2003 | Pacey |
| 2003/0181789 A1 | 9/2003 | Mazzei |
| 2004/0220454 A1 | 11/2004 | Dalle et al. |
| 2005/0240081 A1 | 10/2005 | Eliachar |
| 2007/0175482 A1 | 8/2007 | Kimmel |
| 2007/0287888 A1 | 12/2007 | Lovell |
| 2008/0064926 A1 | 3/2008 | Chen |
| 2008/0208006 A1 | 8/2008 | Farr |
| 2009/0099421 A1 | 4/2009 | Shalman et al. |
| 2009/0299146 A1 | 12/2009 | McGrath |
| 2010/0041955 A1 | 2/2010 | Grey |
| 2010/0081875 A1 | 4/2010 | Fowler |
| 2010/0198009 A1 | 8/2010 | Farr |
| 2011/0028790 A1 | 2/2011 | Farr |

FOREIGN PATENT DOCUMENTS

| | | |
|---|---|---|
| EP | 1166710 A2 | 1/2001 |
| EP | 1598001 A1 | 11/2005 |
| EP | 1640033 A1 | 3/2006 |
| FR | 2381528 A1 | 9/1978 |
| JP | 19935501967 A | 4/1994 |
| JP | 200824221 | 1/1996 |
| JP | 2000184607 | 1/2002 |
| JP | 2002000732 | 1/2002 |
| JP | 200265589 A | 3/2002 |
| JP | 2005520586 | 7/2005 |
| JP | 2006525058 A | 11/2006 |
| JP | 2006326111 | 12/2006 |
| JP | 2006326111 A | 12/2006 |
| JP | 2007117116 A | 5/2007 |
| JP | 2008119305 A | 5/2008 |
| JP | 200853551 | 9/2008 |
| JP | 2008535551 A | 9/2008 |
| JP | 2008289669 A | 12/2008 |
| JP | 2009531133 | 9/2009 |
| WO | 9014041 | 11/1990 |
| WO | 0030707 A2 | 6/2000 |
| WO | 2006102770 A1 | 10/2006 |
| WO | 2007066134 A2 | 6/2007 |
| WO | 2007126657 A1 | 11/2007 |
| WO | 2008157170 A2 | 12/2008 |
| WO | 2009027669 A2 | 3/2009 |

OTHER PUBLICATIONS

Notification of Reason for Refusal in Japanese Patent Application No. 2011-533817, Japanese Patent Office, Jun. 18, 2013.

Notification of Reason for Refusal in Japanese Patent Application No. 2012-505216, Japanese Patent Office, Aug. 14, 2013.

Patent Examination Report No. 1 in Australian patent application No. 2010288342, dated Aug. 22, 2013.

First Office Action in China Patent Application No. 201080043321X.

Notice of Reasons for Rejection in Japanese Patent Application No. 2012-526108, dated Oct. 25, 2013.

GUIDING DEVICE FOR USE WITH LARYNGOSCOPE

FIELD OF THE INVENTION

This invention relates to a guiding device for use with a laryngoscope, more particularly to a guiding device for use with a laryngoscope for assisting in the orotracheal insertion of a tube into a patient.

BACKGROUND OF THE INVENTION

The expression "orotracheal tube" generally designates an endotracheal tube that is inserted through the mouth. Orotracheal intubation consists in inserting a tube through the mouth, the laryngeal inlet and into the trachea of a patient. This procedure is commonly performed in medical conditions in patients who are unable to protect their airways, are at risk of pulmonary aspiration and those that require assistance with mechanical ventilation. It is also commonly performed to permit safe general anaesthesia to enable mechanical ventilation during surgery.

A laryngoscope assists with intubation by allowing the clinician to visualise the path of the endotracheal tube as it passes through the glottis towards the trachea. Tracheal intubation can be performed by direct laryngoscopy or indirect laryngoscopy.

During direct laryngoscopy, a laryngoscope is used to obtain a direct view of the vocal cords. An orotracheal tube is inserted under direct vision through the vocal cords normally in an unconscious patient. A laryngoscope typically comprises a handle and a blade. There are many types of laryngoscopes designed for direct laryngoscopy. The blade may be curved (e.g. the Macintosh blade), straight (e.g. the Miller blade) or may comprise a moveable hinged blade tip (e.g. McCoy laryngoscope).

The technique of orotracheal intubation begins with the blade inserted into the right corner of the patient's mouth. The blade is shaped such that a flange will push the tongue to the left side of the oropharynx to create space in the oropharynx through which a view of the larynx will be sought. The epiglottis is visualised. The laryngoscope handle is manipulated so that the blade lifts the epiglottis directly with the straight blade or indirectly with the curved blade thereby exposing the laryngeal inlet in normal patients. The endotracheal tube is then advanced past the vocal cords into the trachea.

Most intubations are straightforward using the direct laryngoscopy procedure described above. However some patients are known to be difficult to intubate under direct laryngoscopy, especially if there are anatomical abnormalities or if the larynx lies particularly anteriorly. Other patients are unexpectedly found during direct laryngoscopy to be difficult to intubate this way.

Intubation of these patients may be more successful using indirect laryngoscopy. This can be performed using a videolaryngoscope such as those sold under the trademarks Airtraq and GlideScope. These videolaryngoscopes have a light source and imaging modality embedded in or inserted near to the distal portion of the blade. The blade is shaped such that with manipulation the imaging modality can be positioned adjacent to the larynx. This enables visualisation of the laryngeal inlet on a viewer or screen. Fibreoptic intubating laryngoscopes are also used for intubation, particularly if direct laryngoscopy is judged to be difficult or dangerous.

When the user attempts to insert an endotracheal tube, the tip can be visualised on the screen as it passes through the larynx. It is common however with videolaryngoscopes for a good laryngoscopic view on the screen to be achieved but for the user to have difficulty directing the endotracheal tube into the laryngeal inlet. Most problematic is the endotracheal tube tip directing too posteriorly. A stiff introducer or bougie can be inserted into the endotracheal tube to try to overcome this difficulty but this adds complexity and risk to the procedure.

Some videolaryngoscopes, for example the Airtraq® and the Pentax-AWS®, have an insertion technique completely different to that used in direct laryngoscopy and have an open sided rigid channel to help guide the tube. A disadvantage of these rigid open sided channels is that the endotracheal tube is not placed with a technique similar to direct laryngoscopy which is familiar to all anesthesiologists. Another disadvantage is that depending upon tube diameter used, the tube tip is not always gripped sufficiently to direct it along the blade in a sufficiently anterior direction. Another disadvantage is that the rigidity of the guiding channel can impede the removal of the laryngoscope over the endotracheal tube when intubation has been achieved and the laryngoscope needs to be removed.

It is an object of this invention to mitigate problems such as those described above.

SUMMARY OF THE INVENTION

According to a first aspect of the invention, there is provided a guiding device for use with a laryngoscope for assisting in the insertion of an endotracheal tube into a patient, the device comprising a guiding means for guiding an endotracheal tube through the patient's upper airways, and attachment means to attach the guiding means to the blade of the laryngoscope. When the guiding means is attached to the blade of the laryngoscope, the outer shape of the guiding means plus blade may resemble any of the shapes commonly used in laryngoscopy, i.e. the guiding means plus blade may be curved, straight or may comprise a moveable hinged blade tip.

The guiding means is preferably releasably coupled to the endotracheal tube.

The invention is intended to improve the ease of intubation through the patient's mouth and into his upper airways.

The guiding device is preferably integrally constructed and may be one-piece blow moulded so that the cost of production is relatively affordable. However, two-part guiding devices may also be used. The two components of a two-part guiding device may be joined together by welding, gluing or clipping.

The guiding means may be made of a flexible material, such as a flexible thermoplastic material, or of a rigid material. The guiding device, or part of the guiding device, may be flexible due to its shape, design or dimension (e.g. thickness).

The guiding means may be movable relative to the surface of the blade. For example, the guiding means may be attached to the blade or the attachment means by means of one or more hinge elements. An advantage of these features is that they enable the user to adjust the guiding means, making a single guiding device suitable for placing and securing endotracheal tubes of various dimensions to the laryngoscope. In addition, in embodiments in which the guiding means is movable relative to the surface of the blade, the guiding means may be adjusted so that the endotracheal tube or its distal end is deflected towards the surface of the blade to improve visualisation and positioning of the tube in the patient's airways. The guiding device may be designed to enable the guiding means to be adjusted before use and/or during use.

In an alternative embodiment the guiding means is fixed relative to the surface of the blade once the attachment means has secured the guiding means to the laryngoscope. Guiding devices which are fixed relative to the surface of the blade may be easier and cheaper to manufacture, therefore such embodiments may be better suited for use as disposable items.

The guiding means is of dimensions suitable to support and guide the endotracheal tube or to grip the tube. It may be tubular or a portion of a circumference of a tubular channel or a guiding paddle. Most preferably, the guiding means deflects the tube towards the surface of the blade or another part of the that laryngoscope or the guiding device and/or the guiding means deflects the distal tip of the tube towards the distal end of the blade or guiding means into the laryngeal inlet.

In embodiments in which the guiding means comprises a guiding paddle, the guiding paddle provides a surface that the endotracheal tube can glide over towards the laryngeal inlet and into the trachea of a patient. When the guiding device is attached to the laryngoscope, the guiding paddle may extend outwards substantially level to the upper or lower surface of the blade of the laryngoscope.

The guiding means may comprise two guiding paddles, one guiding paddle providing a surface that the endotracheal tube can glide over and the other guiding paddle partially enclosing the endotracheal tube to help prevent displacement of the endotracheal tube during insertion, or one guiding paddle located on one side of the device and the other guiding paddle located on the other side of the device.

In a preferred embodiment, the attachment means comprises a sleeve capable of enclosing, partly or wholly, the blade of the laryngoscope. For example, the sleeve may surround a portion of the length of the blade; or it may comprise a longitudinal slit so that the sleeve may be easily fitted around the blade.

The attachment means may enable reversible attachment of the guiding device to the laryngoscope. Reversible attachment may be enabled using pins, screws or bolts, alone or in combination.

In another embodiment, the guiding device extends longitudinally from the distal end of the blade of the laryngoscope to form an extended tip to provide an improved laryngoscopic view of the patient's airways.

Preferably, the guiding device further comprises one or more channels in which visualisation means can be removably inserted or secured. The visualisation means may comprise part of the laryngoscope or may be independent from but suitable for use with the laryngoscope.

The guiding device may be made, partly or wholly, of a transparent material. The guiding device may be made, partly or wholly, of a disposable material. The disposable material may be plastic or metal.

According to a second aspect of the invention there is provided a laryngoscope comprising a guiding device as described above. The laryngoscope according to the present invention may further comprise indirect means for visualising the laryngeal inlet. For example, the visualisation means may comprise a light source, fibreoptic visualisation means, a camera and/or a display screen. However, the laryngoscope may be used without visualisation means for straightforward cases.

BRIEF DESCRIPTION OF THE FIGURES

For a fuller understanding of the nature and objects of the present invention, reference should be made to the following drawings in which the same reference numerals are used to indicate the same or similar parts wherein.

DESCRIPTION OF PREFERRED EMBODIMENTS

In this application, the terms "distal part" and "proximal part" are used relative to the medical professional, i.e. the "distal part" is used to describe the part of the device that is inserted first into the patient. The terms "anterior" and "posterior" are used relative to the patient to designate his front and his back, respectively.

Figure 1:
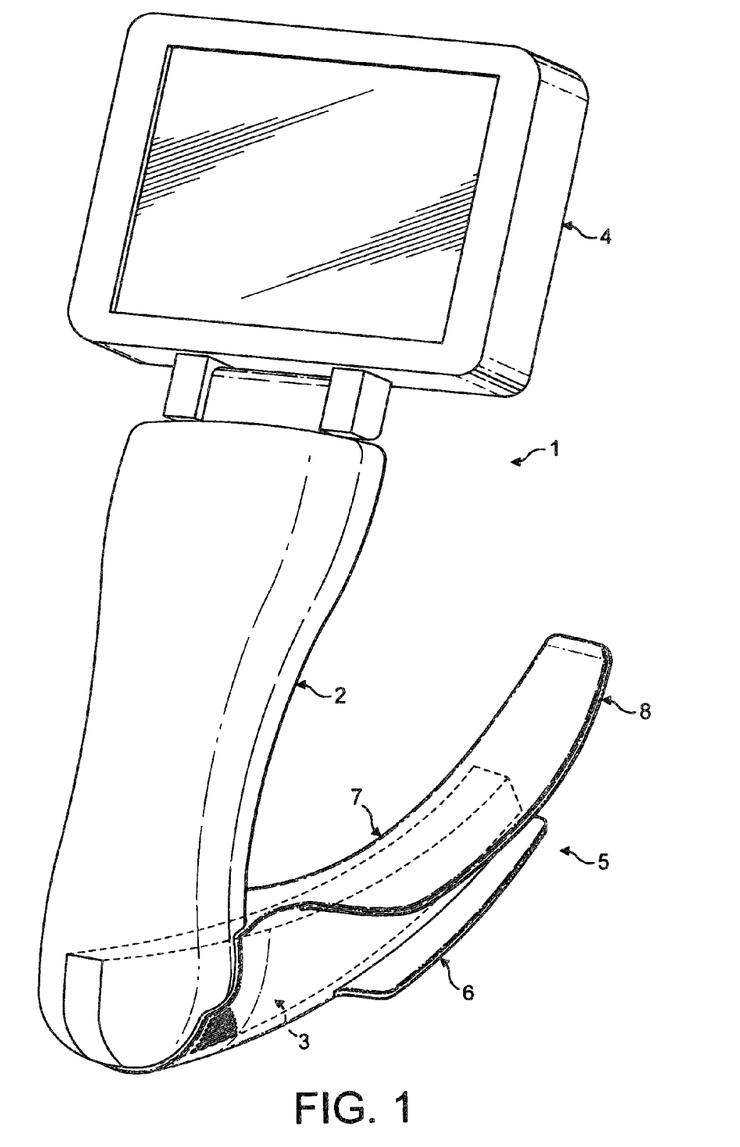
FIG. 1 shows an isometric view of one embodiment of a laryngoscope with a guiding device according to the invention.
Figure 2:
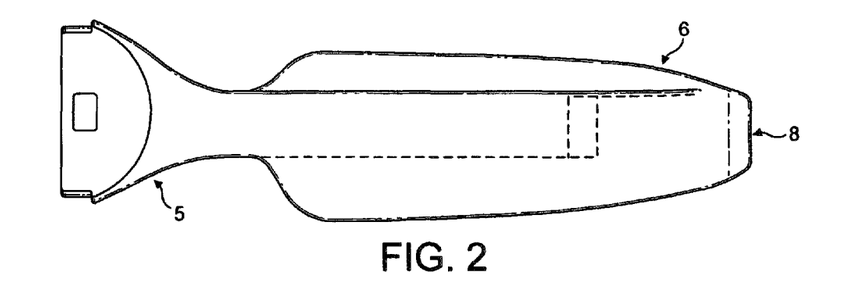
FIG. 2 shows a top view of one embodiment of the guiding device.
Figure 3:
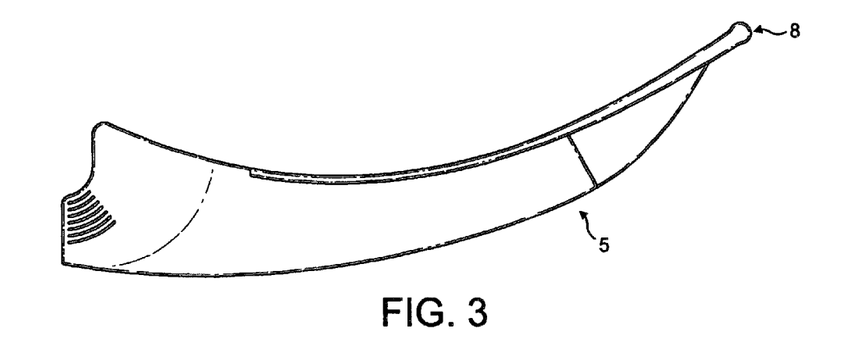
FIG. 3 shows a side view of the guiding device of FIG. 2.
Figure 4:
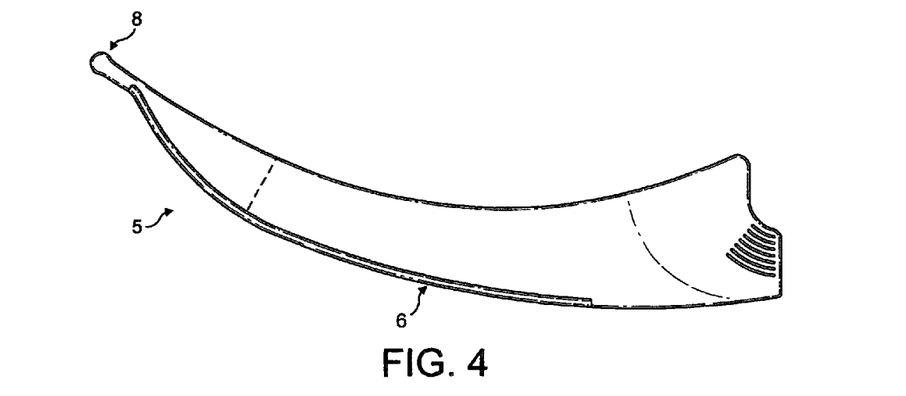
FIG. 4 shows a view of the other side of the guiding device of FIG. 2.
Figure 5:
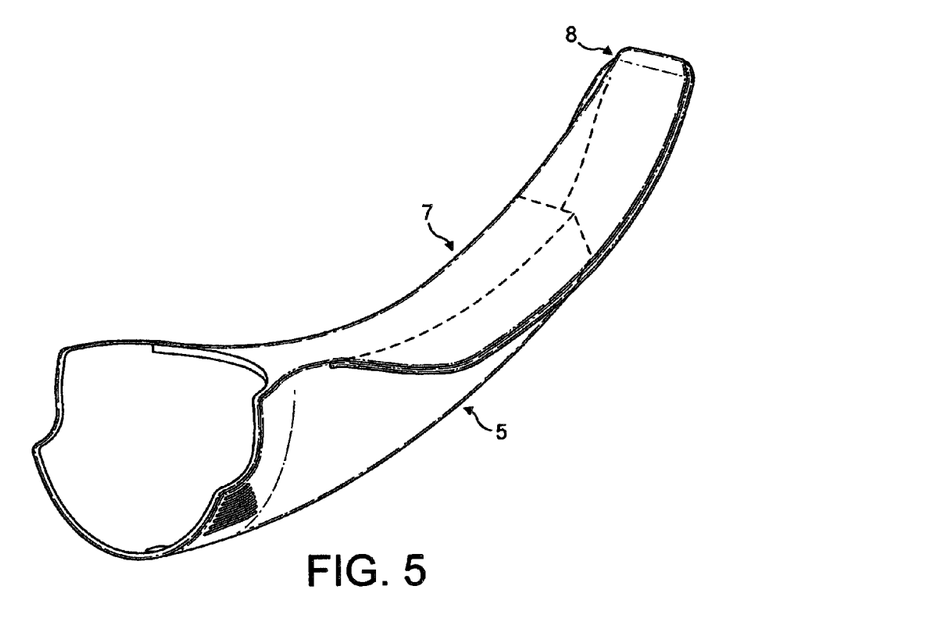
FIG. 5 shows an isometric view of the guiding device of FIG. 2.
Figure 6:
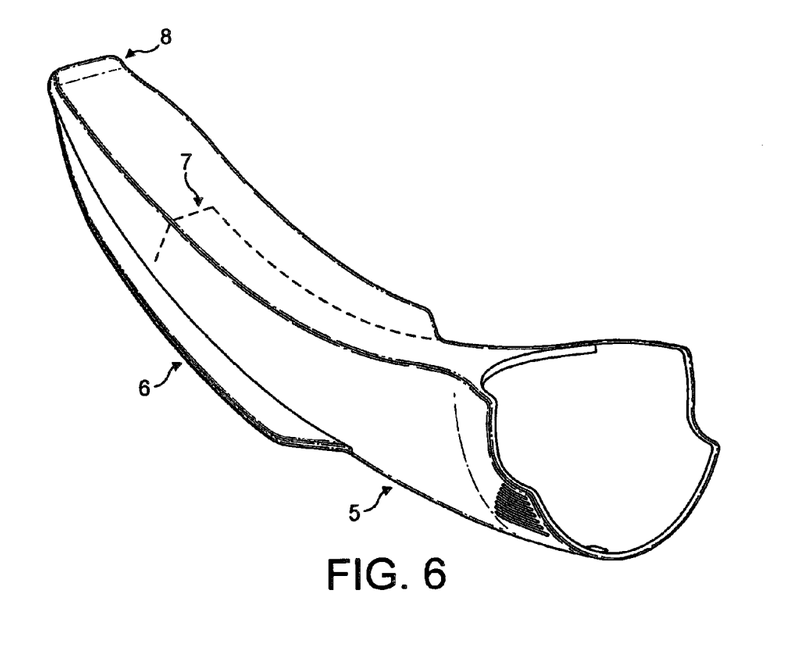
FIG. 6 shows an alternative isometric view of the guiding device of FIG. 2.
Figure 7:
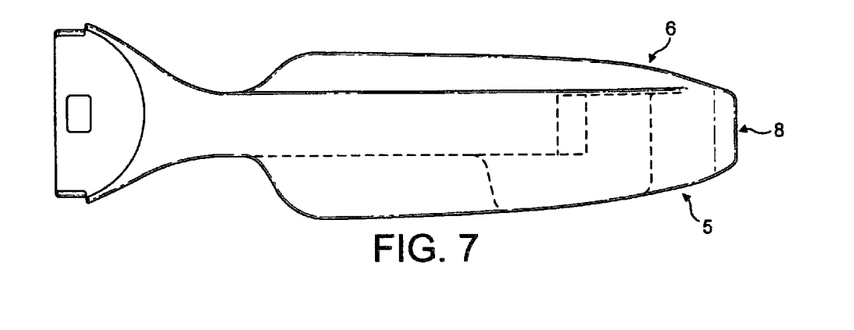
FIG. 7 shows a top view of a second embodiment of the guiding device.
Figure 8:
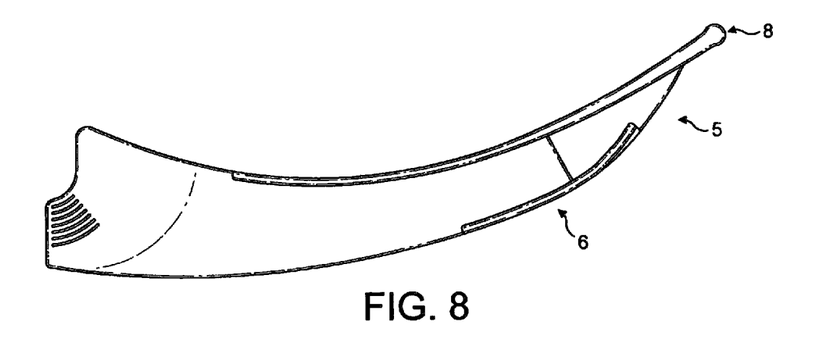
FIG. 8 shows a side view of the guiding device of FIG. 7.
Figure 9:
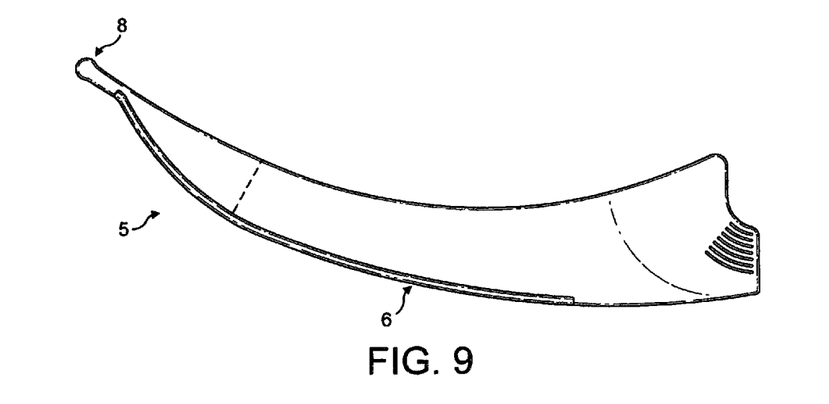
FIG. 9 shows a view of the other side of the guiding device of FIG. 7.
Figure 10:
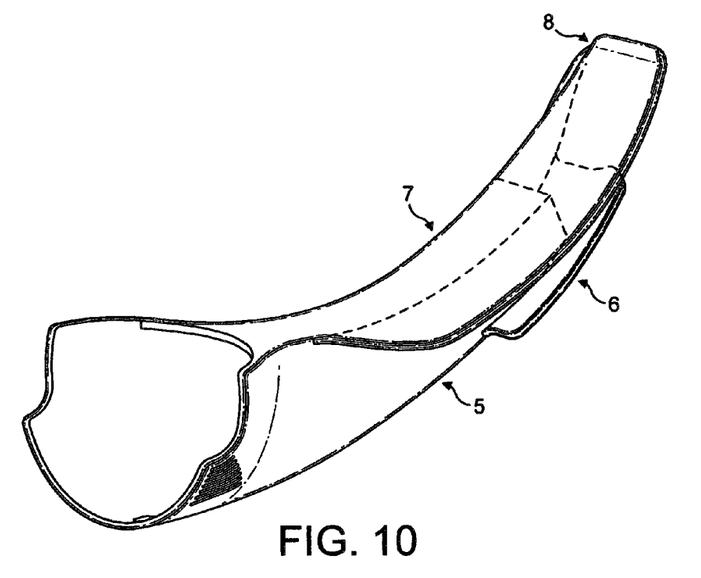
FIG. 10 shows an isometric view of the guiding device of FIG. 7.
Figure 11:
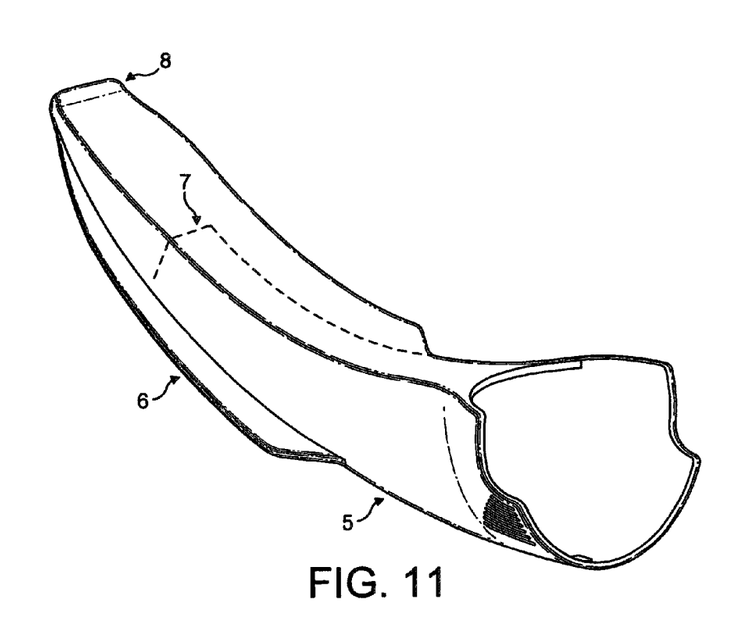
FIG. 11 shows an alternative isometric view of the guiding device of FIG. 7.
Figure 12:
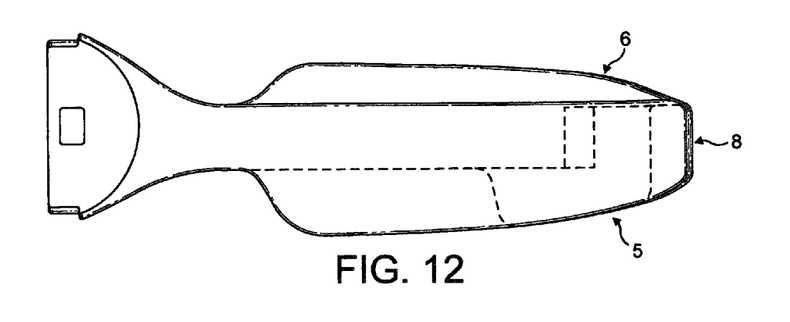
FIG. 12 shows a top view of a second embodiment of the guiding device.
Figure 13:
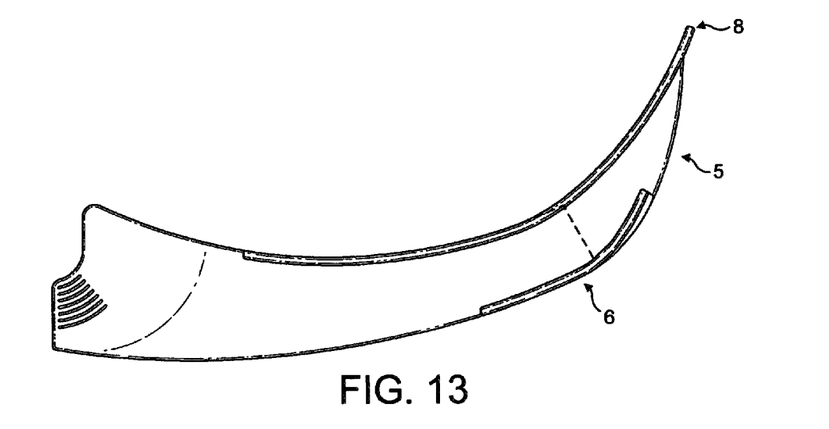
FIG. 13 shows a side view of the guiding device of FIG. 12.
Figure 14:
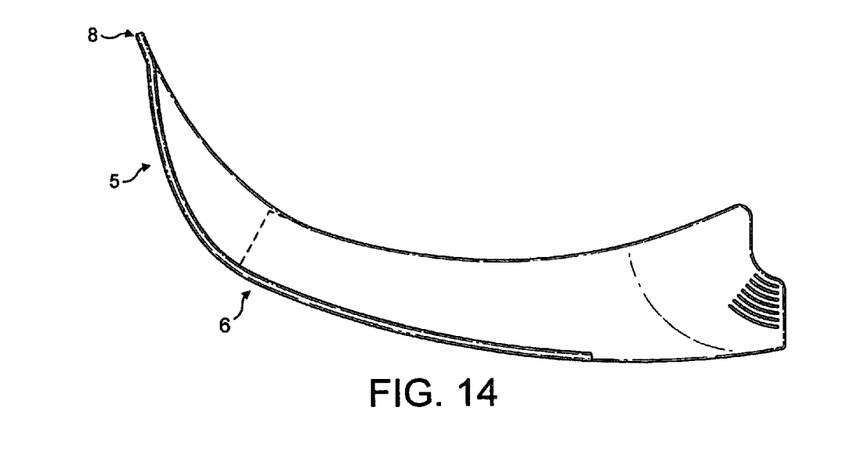
FIG. 14 shows a view of the other side of the guiding device of FIG. 12.
Figure 15:
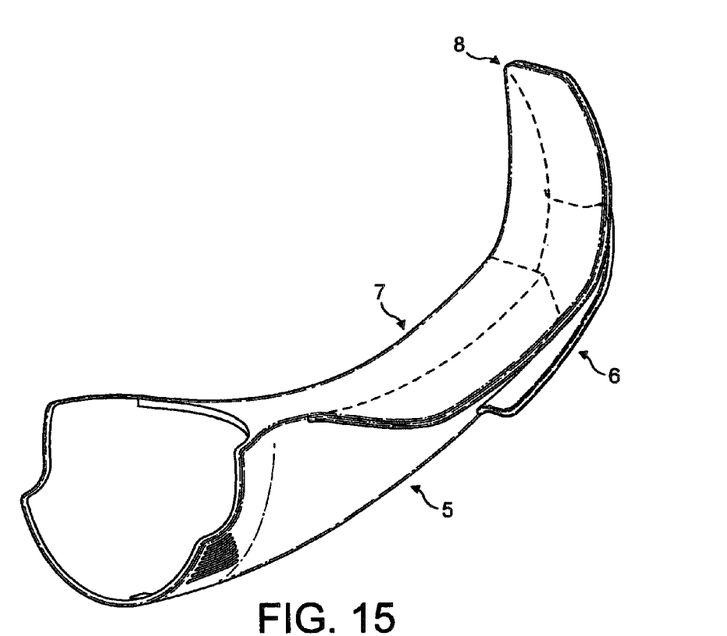
FIG. 15 shows an isometric view of the guiding device of FIG. 12.
Figure 16:
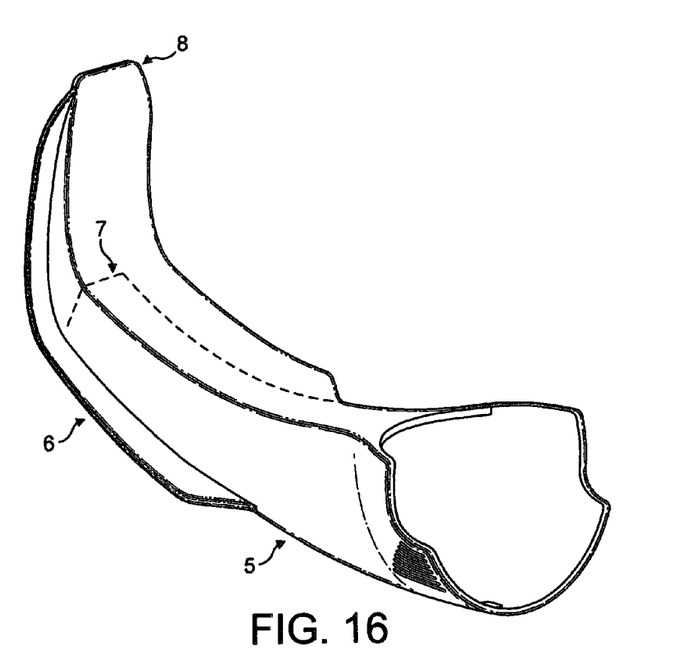
FIG. 16 shows an alternative isometric view of the guiding device of FIG. 12.

The laryngoscope (1) of FIG. 1 comprises a handle (2) for holding and maneuvering the laryngoscope and a rigid blade (3) that is pivotally attached to the handle (2). The laryngoscope (1) further comprises means of visualisation including a display screen (4) to visualise the area captured, for example, by a camera (not shown).

A guiding device (5) is shown that comprises a guiding means (6) for guiding an endotracheal tube through the patient's mouth and upper airways and an attachment means embodied as a sleeve (7).

The blade (3) of the laryngoscope (1) is inserted into the sleeve (7). The sleeve (7) should preferably fit the blade (3) so that it is sufficiently secured during use and so that it can be removed after use.

The guiding means (6) deflects the tube towards the surface of the sleeve (7) and deflects the distal tip of the tube towards the distal end of the blade and into the laryngeal inlet.

Preferably, the guiding means (6) has mechanical and geometric properties or external maneuverability such that it deflects the distal endotracheal tube tip towards the blade and thereafter along a pathway through the glottic opening. The flexibility or maneuverability of the guiding means (6) permits the endotracheal tube to disengage from the blade when intubation has been achieved and the laryngoscope needs removing.

The guiding means (6) may be externally movable relative to the attachment means so that the distal end of the endotracheal tube is pushed along the surface of laryngoscope blade (3). The guiding means (6) may be hinged or be made of a flexible material.

To substantially deflect the distal end of the endotracheal tube along the blade surface there needs to be sufficient force from the guiding means (6). However once tracheal intubation is achieved it is desirable that there is very little force holding the endotracheal tube between the blade (3) and the guiding means (6) because it is desirable to remove the laryngoscope from the patient's upper airway whilst applying minimal forces so as to avoid disrupting the endotracheal tube position or damaging the airway structures.

The guiding means (6) may be hinged, be externally movable or of stiffness sufficient to guide a range of external diameters of endotracheal tubes along the line of the surface of the rigid blade and anteriorly (i.e. at the distal end) into the laryngeal inlet under indirect vision.

The guiding means (6) may be flexible enough such that the endotracheal tube can slip out laterally easily when the laryngoscope needs to be removed following intubation.

The blade (3) may be straight, e.g. a Miller laryngoscope blade. Alternatively, a curved blade may be used, e.g. a Macintosh blade. Another suitable type of blade is one that comprises a moveable and/or hinged blade tip, e.g. McCoy laryngoscope.

FIG. 1 shows a straight blade (3) and a guiding device (5) that extends longitudinally from the distal end of the blade (3) to form an extended tip or tongue (8). This guiding device (5) is particularly suitable for indirect videolaryngoscopy and the tip (8) facilitates a good laryngoscopic view for the user, for example, on a display screen (4).

An important advantage of the guiding device (5), and in particular of the use of an attachment means, is that it may be used in combination with any type of laryngoscope, including those with straight, curved, angled or hinged blades as described above, and can therefore be used as a universal guiding means (6). Furthermore, the guiding means (6) may include a tip (8) that may be straight, curved or angled to modify an existing laryngoscope blade. For example, a guiding means with a straight tip may be used with a Miller laryngoscope to extend the length of the existing blade; a guiding means with a curved tip may be used with a straight blade to transform it into a Macintosh-type blade.

The guiding device (5) may be reusable, disposable, partly reusable or partly disposable. Prior art reusable laryngoscopes must be cleaned and sterilised after use and the process is time consuming and incur costs. Clinicians may use a disposable sheath to cover the blade of a laryngoscope to minimise the need for cleaning and sterilisation. Alternatively, a reusable laryngoscope or a reusable blade may be used but are more costly to produce than a disposable or partly disposable guiding device (5).

The laryngoscope (1) may comprise visualisation means such as a light source, fibreoptics, camera or other technology that enable external indirect visualisation of the laryngeal inlet. Indirect visualisation of the laryngeal inlet through fibreoptics, camera or other means, is particularly useful to assist the user to juxtapose the tip of the blade with the laryngeal inlet.

In a preferred embodiment, the laryngoscope (1) may consist of a disposable sleeve (7) and separate reusable camera and light source components (not shown). The disposable sleeve (7) may comprise a channel for the camera or light source component to be inserted prior to use and removed from after use. For example in the laryngoscope of FIG. 1, a camera and a light source are located at the distal end of the blade (3) and are protected from bodily fluids by the disposable sleeve (7).

It may be desirable that the guiding means (6) is partly or wholly transparent so as no to impede the line of view from the camera or similar to the laryngeal inlet. For example, the distal section of the channel where the camera is positioned may be transparent to permit visualisation. Similarly, where the guiding device (5) comprises a distal extension (8), the extension may be transparent for improved visualisation of the patient's airways. In a preferred embodiment, the whole guiding device (5) may be made out of a transparent material.

In use, the guiding device (5) may be attached to the laryngoscope (1) by inserting the blade (3) into the sleeve (7). The endotracheal tube may be attached to the guiding means (6) that positions the tube along the surface of the blade (3) or along the surface of the sleeve (7). The distal end of the tube may be positioned so that its distal tip aligns with the distal end of the blade (3). The laryngoscope (1) is inserted into the mouth of the patient. The blade (3) will push the tongue of the patient to the side of the oropharynx to create space through which the larynx and the epiglottis can be viewed. The blade is manipulated to lift the epiglottis thereby exposing the laryngeal inlet. The endotracheal tube can then be advanced past the vocal cords into the trachea. The user can visualise the distal end of the blade for example on the display screen (4) and manipulate the laryngoscope accordingly. Once the tube is correctly positioned, it is released from the guiding device (5) without displacing the tube and without damage to the surrounding tissues.

The size and shape of guiding devices (5) according to the present invention can vary. In particular, the size and shape of the guiding devices (5) may vary to suit a patient's anatomy. In the embodiment depicted in FIG. 1, the laryngoscope (1) and blade (3) are reusable whilst the guiding device (5) is disposable. This enables the laryngoscope (1) and its blade (3) to be used with a number of patients, whilst a different guiding device (5) is used with each patient. Therefore, the clinician is free to choose the size and shape of guiding device (5) best suited to use with an individual patient.

FIGS. 2 to 6 depict a guiding device (5) with a guiding means (6) in the form of a single guiding paddle extending outwards substantially level to the lower surface of the laryngoscope blade (3). The embodiment of FIGS. 2 to 6 includes attachment means in the form of a sleeve (7) that may be reversibly attached to the laryngoscope blade (3).

FIGS. 7 to 11 depict an alternative embodiment of a guiding device (5) with a guiding means (6) in the form of two guiding paddles, each extending outwards substantially level to the lower surface of the laryngoscope blade (3) but on different sides of the guiding device (5). One of the guiding paddles extends under the upper surface of the guiding device (5) to partially enclose an endotracheal tube located between the two surfaces.

FIGS. 12 to 16 depict another alternative embodiment of a guiding device (5), in which the extended tip (8) is anteriorly deflected to enable an endotracheal tube inserted using the device (5) to be deflected anteriorly.

The invention claimed is:

1. A guiding device for use with a laryngoscope having a blade for assisting in the insertion of an endotracheal tube into a patient, the device comprising a guiding paddle for guiding the endotracheal tube through the patient's upper airways, and attachment means to attach the guiding paddle to the blade of the laryngoscope such that the guiding paddle extends outward substantially level to and in the plane of the upper or lower surface of the blade of the laryngoscope.

2. The guiding device according to claim 1, wherein the guiding paddle is releasably coupled to the endotracheal tube.

3. The guiding device according to claim 2, wherein the guiding paddle is made of a flexible material.

4. The guiding device according to claim 1, wherein the guiding paddle is movable relative to a surface of the blade.

5. The guiding device according to claim 4, wherein the guiding paddle is attached to the blade or the attachment means by means of one or more hinge elements.

6. The guiding device according to claim 1, wherein the attachment means comprises a sleeve capable of enclosing, partly or wholly, the blade of the laryngoscope.

7. The guiding device according to claim 1, wherein the device extends longitudinally from a distal end of the blade of the laryngoscope to form an extended tip.

8. The guiding device according to claim 1, the device further comprises one or more channels in which visualisation means can be secured or removably inserted.

9. The guiding device according to claim 1, wherein the guiding device is made, partly or wholly, of a transparent material.

10. The guiding device according to claim 1, wherein the guiding device is made, partly or wholly, of a disposable material.

11. The guiding device according to claim 1, further comprising a second guiding paddle, the guiding paddle providing a surface that the endotracheal tube can glide over and the second guiding paddle partially enclosing the endotracheal tube to help prevent displacement of the endotracheal tube during insertion.

12. The guiding device according to claim 1, further comprising a second guiding paddle, the guiding paddle located on one side of the device and the second guiding paddle located on the other side of the device.

13. A laryngoscope comprising a guiding device according to claim 1.

14. The laryngoscope according to claim 13 further comprising indirect means for visualising the laryngeal inlet.

15. The laryngoscope according to claim 14, wherein the visualisation means comprises a light source, fibreoptic visualisation means, a camera and/or a display screen.

16. A guiding device for use with a laryngoscope having a blade for assisting in the insertion of an endotracheal tube into a patient, the guiding device comprising:
    a sleeve for enclosing, partly or wholly, the blade of the larnyngoscope; and
    a guiding paddle attached to the sleeve for guiding the endotracheal tube through the patient's upper airways, the guiding paddle having a surface extending outward substantially level to and in the plane of a lower surface of the blade.

17. The guiding device of claim 16, further comprising a second guiding paddle partially enclosing the endotracheal tube to help prevent displacement of the endotracheal tube during insertion.

18. The guiding device of claim 16, wherein the guiding paddle is positioned on a first side of the device, and the device further comprises a second guiding paddle positioned on a second side of the device opposite the first side.

19. The guiding device of claim 16, wherein the device extends longitudinally form the distal end of the blade of the laryngoscope to form an extended tip, the extended tip being anteriorly deflected.

* * * * *